(12) United States Patent  
Su et al.

(10) Patent No.: US 11,779,222 B2
(45) Date of Patent: Oct. 10, 2023

(54) METHOD OF AND IMAGING SYSTEM FOR CLINICAL SIGN DETECTION

(71) Applicants: Tung-Hung Su, Taipei (TW); Cheng-Fu Chou, Taipei (TW); Shann-Ching Chen, Taipei (TW)

(72) Inventors: Tung-Hung Su, Taipei (TW); Cheng-Fu Chou, Taipei (TW); Shann-Ching Chen, Taipei (TW)

(73) Assignees: COMPAL ELECTRONICS, INC., Taipei (TW); National Taiwan University Hospital, Taipei (TW)

( * ) Notice: Subject to any disclaimer, the term of this patent is extended or adjusted under 35 U.S.C. 154(b) by 391 days.

(21) Appl. No.: 16/924,202

(22) Filed: Jul. 9, 2020

(65) Prior Publication Data

US 2021/0007606 A1    Jan. 14, 2021

Related U.S. Application Data

(60) Provisional application No. 62/872,695, filed on Jul. 10, 2019.

(51) Int. Cl.
*A61B 5/00* (2006.01)
*G06T 7/00* (2017.01)
(Continued)

(52) U.S. Cl.
CPC .......... *A61B 5/0077* (2013.01); *A61B 5/0035* (2013.01); *A61B 5/0075* (2013.01);
(Continued)

(58) Field of Classification Search
CPC ... A61B 5/0077; A61B 5/0035; A61B 5/0075; A61B 5/015; A61B 5/14546;
(Continued)

(56) References Cited

U.S. PATENT DOCUMENTS 6,550,933 B1  4/2003  Panz
7,283,106 B2  10/2007  Allen et al.
(Continued)

FOREIGN PATENT DOCUMENTS

CN       1758257      4/2006
CN     101828905      9/2010
(Continued)

OTHER PUBLICATIONS

Andre Esteva et al., "Dermatologist-level classification of skin cancer with deep neural networks", Nature, vol. 542, Feb. 2017, pp. 1-11.
(Continued)

*Primary Examiner* — Eric F Winakur
*Assistant Examiner* — Abid A Mustansir
(74) *Attorney, Agent, or Firm* — JCIPRNET

(57) ABSTRACT

The disclosure provides a method of and an imaging system for clinical sign detection. The method uses an imaging system having an RGB image sensor and the processing device disclosed herein. An image of a patient or examinee is captured by the RGB image sensor to generate an RGB image. Clinical signs of the patient or examinee are detected by the processing device based on the RGB images.

20 Claims, 15 Drawing Sheets

(51) Int. Cl.

| | | |
|---|---|---|
| *G06T 7/80* | (2017.01) | |
| *G06T 7/90* | (2017.01) | |
| *A61B 5/145* | (2006.01) | |
| *A61B 5/01* | (2006.01) | |
| *A61B 5/1455* | (2006.01) | |
| *G16H 30/40* | (2018.01) | |
| *H04N 23/10* | (2023.01) | |
| *H04N 23/56* | (2023.01) | |

(52) U.S. Cl.
CPC .......... *A61B 5/015* (2013.01); *A61B 5/14546* (2013.01); *A61B 5/14551* (2013.01); *A61B 5/443* (2013.01); *A61B 5/7267* (2013.01); *A61B 5/7278* (2013.01); *A61B 5/7282* (2013.01); *A61B 5/7485* (2013.01); *G06T 7/0012* (2013.01); *G06T 7/80* (2017.01); *G06T 7/90* (2017.01); *G16H 30/40* (2018.01); *H04N 23/10* (2023.01); *H04N 23/56* (2023.01); *A61B 2562/0257* (2013.01); *A61B 2576/00* (2013.01); *G06T 2207/10024* (2013.01); *G06T 2207/10036* (2013.01); *G06T 2207/10048* (2013.01); *G06T 2207/20081* (2013.01); *G06T 2207/20084* (2013.01); *G06T 2207/30196* (2013.01)

(58) Field of Classification Search
CPC ... A61B 5/14551; A61B 5/443; A61B 5/7267; A61B 5/7278; A61B 5/7282; A61B 5/7485; A61B 2562/0257; A61B 2576/00; G06T 7/0012; G06T 7/80; G06T 7/90; G06T 2207/10024; G06T 2207/10036; G06T 2207/10048; G06T 2207/20081; G06T 2207/20084; G06T 2207/30196; G06T 2207/30088; G16H 30/40; G16H 50/20; H04N 5/2256; H04N 9/045

See application file for complete search history.

(56) References Cited

U.S. PATENT DOCUMENTS

| | | | |
|---|---|---|---|
| 9,504,428 | B1 | 11/2016 | Gelbman et al. |
| 9,750,420 | B1 | 9/2017 | Agrawal et al. |
| 9,788,917 | B2 | 10/2017 | Mah |
| 9,848,780 | B1 | 12/2017 | DeBusschere et al. |
| 9,992,409 | B2 | 6/2018 | Anzue et al. |
| 10,052,026 | B1 | 8/2018 | Tran |
| 10,390,770 | B2 | 8/2019 | Allen et al. |
| 10,579,203 | B2 | 3/2020 | Zamir et al. |
| 2008/0139966 | A1 | 6/2008 | Zhang et al. |
| 2009/0226059 | A1* | 9/2009 | Levenson ................ G01N 1/30 382/128 |
| 2012/0283573 | A1 | 11/2012 | Gong et al. |
| 2014/0221847 | A1* | 8/2014 | Dubielczyk ........ A61B 5/02055 600/479 |
| 2014/0320611 | A1 | 10/2014 | Choi |
| 2016/0157725 | A1* | 6/2016 | Munoz ................ H04N 5/2256 600/407 |
| 2016/0206216 | A1* | 7/2016 | Kirenko ............ A61B 5/02055 |
| 2016/0210746 | A1 | 7/2016 | Matsuda |
| 2017/0178220 | A1 | 6/2017 | Chong et al. |
| 2017/0319148 | A1 | 11/2017 | Shahin et al. |
| 2018/0289334 | A1 | 10/2018 | De Brouwer et al. |
| 2019/0046099 | A1* | 2/2019 | Lee .................... A61B 5/055 |
| 2019/0213309 | A1* | 7/2019 | Morestin ............ G06V 40/166 |

FOREIGN PATENT DOCUMENTS

| | | |
|---|---|---|
| CN | 102103662 | 6/2011 |
| CN | 101496715 | 12/2012 |
| CN | 101999879 | 1/2013 |
| CN | 103249353 | 8/2013 |
| CN | 104825136 | 8/2015 |
| CN | 105764408 | 7/2016 |
| CN | 106691388 | 5/2017 |
| CN | 102711603 | 7/2017 |
| TW | I296110 | 4/2008 |
| TW | 201301075 | 1/2013 |
| TW | I492737 | 7/2015 |
| TW | I627940 | 7/2018 |
| TW | M569679 | 11/2018 |
| TW | 201902411 | 1/2019 |
| WO | 2013116316 | 8/2013 |
| WO | 2017111606 | 6/2018 |

OTHER PUBLICATIONS

Tsai et al, "Skin Imaging Detection Method Applied to the Analysis of Human Blood Oxygen Concentration" , The 13th National AOI Forum and Exhibition, Mar. 2018, with English translation thereof, pp. 1-12.

Office Action of Taiwan Counterpart Application, dated Apr. 7, 2021, pp. 1-20.

Gladimir V. G. Baranoski et al., "Assessing the sensitivity of human skin hyperspectral responses to increasing anemia severity levels." J. of Biomedical Optics, vol. 20, No. 9, 095002, Sep. 2015, pp. 1-15.

Haiwei Xie et al., "Relationship between dynamic infrared thermal images and blood perfusion rate of the tongue in anaemia patients." Infrared Physics & Technology, vol. 89, Mar. 2018, pp. 27-34.

Anna-Marie Hosking et al., "Hyperspectral Imaging in Automated Digital Dermoscopy Screening for Melanoma." Lasers Surg Med, vol. 51, No. 3, Mar. 2019, pp. 214-222.

Cila Herman, "The role of dynamic infrared imaging in melanoma diagnosis." Expert Rev Dermatol., vol. 8, No. 2, Apr. 1, 2013, pp. 1-12.

Mirwaes Wahabzada et al., "Monitoring wound healing in a 3D wound model by hyperspectral imaging and efficient clustering." PLoS One , vol. 12, No. 12, 2017, pp. 1-14.

Erica Y. Xue et al., "Use of FLIR One Smartphone Thermography in Burn Wound Assessment." Annals of Plastic Surgery, vol. 80, Feb. 1, 2018, pp. 1-3.

Peter H Lin et al., "Infrared thermography in the diagnosis and management of vasculitis." J Vasc Surg Cases Innov Tech., vol. 3, No. 3, Jul. 4, 2017, pp. 112-114.

Mie Jin Lim et al., "Digital Thermography of the Fingers and Toes in Raynaud's Phenomenon." J Korean Med Sci., vol. 29, No. 4, 2014, pp. 502-506.

Marcinkevics, Z. et al., "Hyperspectral evaluation of skin blood oxygen saturation at baseline and during arterial occlusion." Proceedings of SPIE, vol. 10685, 2018, pp. 1-9.

Chi-Lun Huang et al., "The application of infrared thermography in evaluation of patients at high risk for lower extremity peripheral arterial disease." J Vasc Surg., vol. 54, No. 4, Oct. 2011, pp. 1074-1080.

Matija Milanic et al., "Hyperspectral imaging for detection of arthritis: feasibility and prospects." J Biomed Opt., vol. 20, No. 9, Sep. 2015, pp. 1-10.

R Lasanen et al., "Thermal imaging in screening of joint inflammation and rheumatoid arthritis in children." Physiol Meas., vol. 36, No. 2, Feb. 2015, pp. 273-282.

Norimichi Tsumura et al., "Image-based skin color and texture analysis/synthesis by extracting hemoglobin and melanin information in the skin." ACM SIGGRAPH 2003, pp. 770-779.

Romesh P. Nalliah et al., "Students distracted by electronic devices perform at the same level as those who are focused on the lecture." PeerJ, vol. 2, No. 12, Sep. 2014, pp. 1-8.

Lou Gevaux et al., "Three-dimensional hyperspectral imaging: A new method for human face acquisition." Material Appearrance in Electronic Imaging 2018, Jan. 2018, pp. 1-11.

Alvin Rajkomar et al., "Scalable and accurate deep learning with electronic health records." npj Digital Medicine, vol. 1, No. 18, May 8, 2018, pp. 1-10.

(56) References Cited

OTHER PUBLICATIONS

Joshua C Mandel et al., "SMART on FHIR: a standards-based, interoperable apps platform for electronic health records." J Am Med Inform Assoc., Sep. 2016, vol. 23, No. 5, pp. 899-908.
Yinghao Huang et al., "Machine Learning for Medical Examination Report Processing." Real World Data Mining Applications, Annals of Information Systems, vol. 17, 2015, pp. 271-295.

* cited by examiner

METHOD OF AND IMAGING SYSTEM FOR CLINICAL SIGN DETECTION

CROSS-REFERENCE TO RELATED APPLICATION

This application claims the priority benefit of U.S. provisional application Ser. No. 62/872,695, filed on Jul. 10, 2019. The entirety of the above-mentioned patent application is hereby incorporated by reference herein and made a part of this specification.

TECHNICAL FIELD

The disclosure relates to a technique for clinical sign detection.

BACKGROUND

In modern medicine, inspection and observation are the first step of clinical examination by healthcare professionals. General observations begin at the first encounter with a patient or examinee and the health professionals and continue through the whole process of physical examination.

SUMMARY OF THE DISCLOSURE

A method of and an imaging system for clinical sign detection are disclosed.

According to one of the exemplary embodiments, the method is applied to an imaging system having an RGB image sensor and a processing device. The method includes the following steps. An image of a patient or examinee is captured by the RGB image sensor to generate an RGB image. Clinical signs of the patient or examinee are detected by the processing device based on the RGB image.

According to one of the exemplary embodiments, the imaging system includes an RGB image sensor and a processing device having a memory and a processor. The RGB image sensor is configured to capture an RGB image of a patient or examinee to generate an RGB image. The memory is configured to store data. The processor is configured to detect clinical signs of the patient or examinee based on the RGB image.

In order to make the aforementioned features and advantages of the disclosure comprehensible, some embodiments accompanied with figures are described in detail below. It is to be understood that both the foregoing general description and the following detailed description are exemplary, and are intended to provide further explanation of the disclosure as claimed.

It should be understood, however, that this summary may not contain all the aspects and embodiments of the disclosure and is therefore not meant to be limiting or restrictive in any manner. Also, the disclosure would include improvements and modifications which are obvious to one skilled in the art.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

Figure 1:
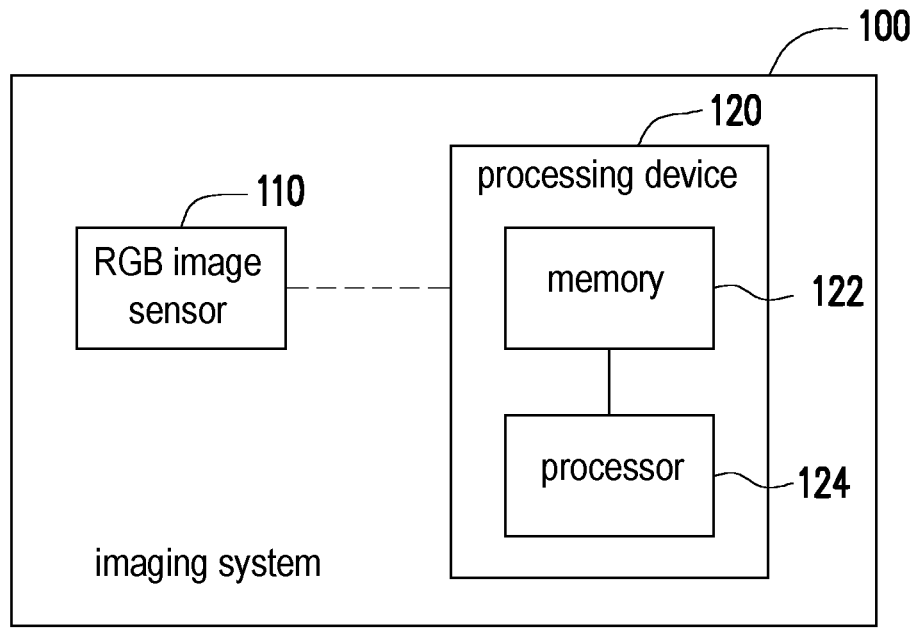
FIG. 1 illustrates a schematic diagram of an imaging system in accordance with one of the exemplary embodiments of the disclosure.

To make the above features and advantages of the application more comprehensible, several embodiments accompanied with drawings are described in detail as follows.

DESCRIPTION OF THE EMBODIMENTS

The advances of digital health enable a paradigm shift from precision medicine to precision health. It is desirable and beneficial for a user to monitor his or her wellness and health condition whenever possible.

As described herein, inspections, observations, and examinations are within the scope of the present disclosure that are implemented through the use of the methods and systems disclosed herein. The conditions of examinee, including development, nutritional status, body figure, physical status, mentality, facial expression, position and posture, can be evaluated. Goal-directed inspection for specific body parts provide crucial information and signs which help the clinical reasoning and diagnosis.

The inspection usually starts from the HEENT examination, which principally concerns the head, eyes, ears, nose, throat/mouth and neck ("HEENT examination"). The hand, extremities and skin also provide important clues to evaluate the underlying chronic illness or acute conditions. The external manifestation of certain illness can be visualized by a detailed inspection, even without specific equipment. The information obtained through inspection may be thoughtfully integrated with the patient's medical history and current health condition.

The observation includes the identification of landmarks of body, measurement the size, relative location to other landmarks, the shape, position, alignment, color, symmetry, and unusual features. A longer visual observation helps to detect movement problems, and respiratory pattern of examinees.

In modern medicine, inspection and observation are the first step of clinical examination, which usually starts from the HEENT examination. However, the inspection is subjective to a physician's experience and usually requires years of training and clinical practices. Besides, self-monitoring is important in examinees with acute illness or chronic diseases, and in regions or situations with limited accessibility to health care.

In the disclosure, an objective and effective self-inspection, an imaging system and a method would be proposed to detect informative clinical signs that reveal early, subtle but critical information related to an examinee's health condition. The information would help the healthcare providers or the users to identify abnormal physical signs related to health condition or certain diseases, and would discover new physical signs before the onset of diseases.

Some embodiments of the disclosure will now be described more fully hereinafter with reference to the accompanying drawings, in which some, but not all embodiments of the application are shown. Indeed, various embodiments of the disclosure may be embodied in many different forms and should not be construed as limited to the embodiments set forth herein; rather, these embodiments are provided so that this disclosure will satisfy applicable legal requirements. Like reference numerals refer to like elements throughout. Also, it should be noted that the terms "patient" and "examinee" are used interchangeably throughout the disclosure.

FIG. 1 illustrates a schematic diagram of an imaging system in accordance with one of the exemplary embodiments of the disclosure. Some selected components of the image processor and their configurations are first introduced in FIG. 1. The functionalities of the components are disclosed in more detail in conjunction with FIG. 2.

Referring to FIG. 1, an imaging system 100 would include an RGB image sensor 110 and a processing device 120. The processing device 120 would include a memory 122 and a processor 124. The memory 122 would be configured to store data including images, programming codes, setting values or the like, and may be, for example, a stationary or mobile device in any form such as a random access memory (RAM), a read-only memory (ROM), a flash memory, a hard drive or other similar devices, integrated circuits or a combination of the above.

In some embodiments, the processor 124 would be configured to perform clinical sign detection and may be one or more of a North Bridge, a South Bridge, a field programmable array (FPGA), a programmable logic device (PLD), an application specific integrated circuit (ASIC), or other similar device or a combination thereof. In some embodiments, the processor 124 may also be a central processing unit (CPU), a programmable general purpose or special purpose microprocessor, a digital signal processor (DSP), a graphics processing unit (GPU), other similar devices, integrated circuits, or a combination thereof.

In one exemplary embodiment, the RGB image sensor 110 and the processing device 120 may be integrated in the imaging system 100 as an all-in-one device such as a smart phone, a tablet computer, and so forth. In another exemplary embodiment, the processing device 120 may be a desktop computer, a laptop computer, a server computer, a tabular computer, a work station, a cloud storage and computation device, or a computer system or a platform that is able to wired or wirelessly connected to the RGB image sensor 110 through a communication interface. In some embodiments, the communication interface may be a transmission interface that is compatible to any wired connection or wireless communication standard to transmit data with other devices.

Figure 2:
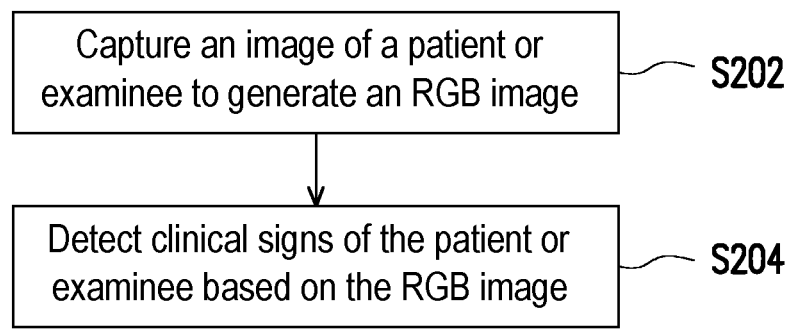
FIG. 2 illustrates a flowchart of a method of clinical sign detection in accordance with one of the exemplary embodiments of the disclosure.

FIG. 2 illustrates a flowchart of a method of clinical sign detection in accordance with one of the exemplary embodiments of the disclosure. In some embodiments, the steps of FIG. 2 may be implemented by the imaging system 100 as illustrated in FIG. 1.

Referring to FIG. 2 in conjunction to FIG. 1, the RGB image sensor 110 would capture an image of a patient or examinee to generate an RGB image (Step S202). Herein, the RGB image sensor 110 may acquire the RGB image of a facial or body part of the examinee. Next, the processor 124 of the processing device 120 would detect clinical signs of the patient or examinee based on the RGB image (Step S204). In one exemplary embodiment, the processor 124 may set the RGB image as input data with a dimension of $M_{RGB} \times N_{RGB} \times 3$ pixels for detecting the clinical signs of the examinee. In another exemplary embodiment, the processor 124 may further extract melanin components and hemoglobin components from the RGB image by using an independent-component analysis (ICA) technique to generate a melanin image and a hemoglobin image, and set the RGB image along with the melanin image and the hemoglobin image as input data with a dimension of $M_{RGB} \times N_{RGB} \times 5$ pixels for detecting the clinical signs of the examinee. Once the input data is collected, the processor 124 may identify regions of interests (ROIs) in which the clinical signs would exist based on knowledge from modern western and Chinese medicine. In one exemplary embodiment, the processing 124 would further associate the clinical signs of the patient or examinee with his/her medical record. Specific examples would be illustrated hereafter.

Figure 3:
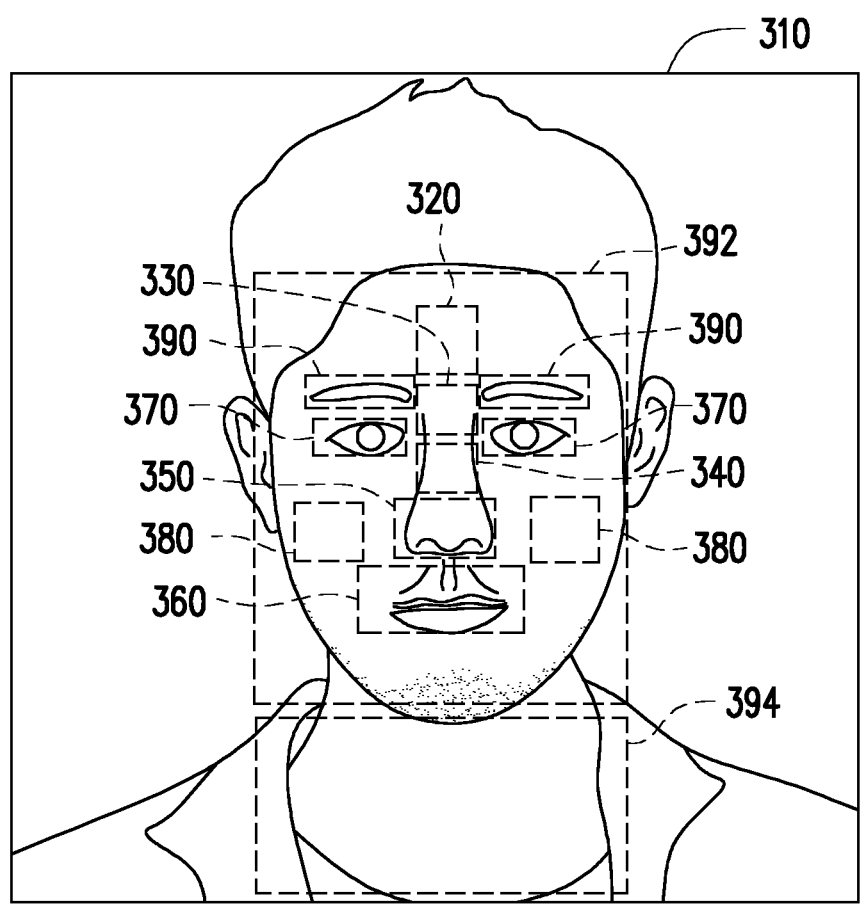
FIG. 3 illustrates ROI identification from a frontal face image in accordance with one of the exemplary embodiments of the disclosure.

FIG. 3 illustrates ROI identification from a frontal face image in accordance with one of the exemplary embodiments of the disclosure.

Referring to FIG. 3, several ROIs may be identified from a frontal face image 310. The ROIs in the frontal face image 310 may include forehead 320, nasion 330, bridge 340, nose tip and nasal wing 350, mouth 360, eyes and sclera 370, cheek 380, eyebrow 390, whole face 392, and neck 394.

Figure 4:
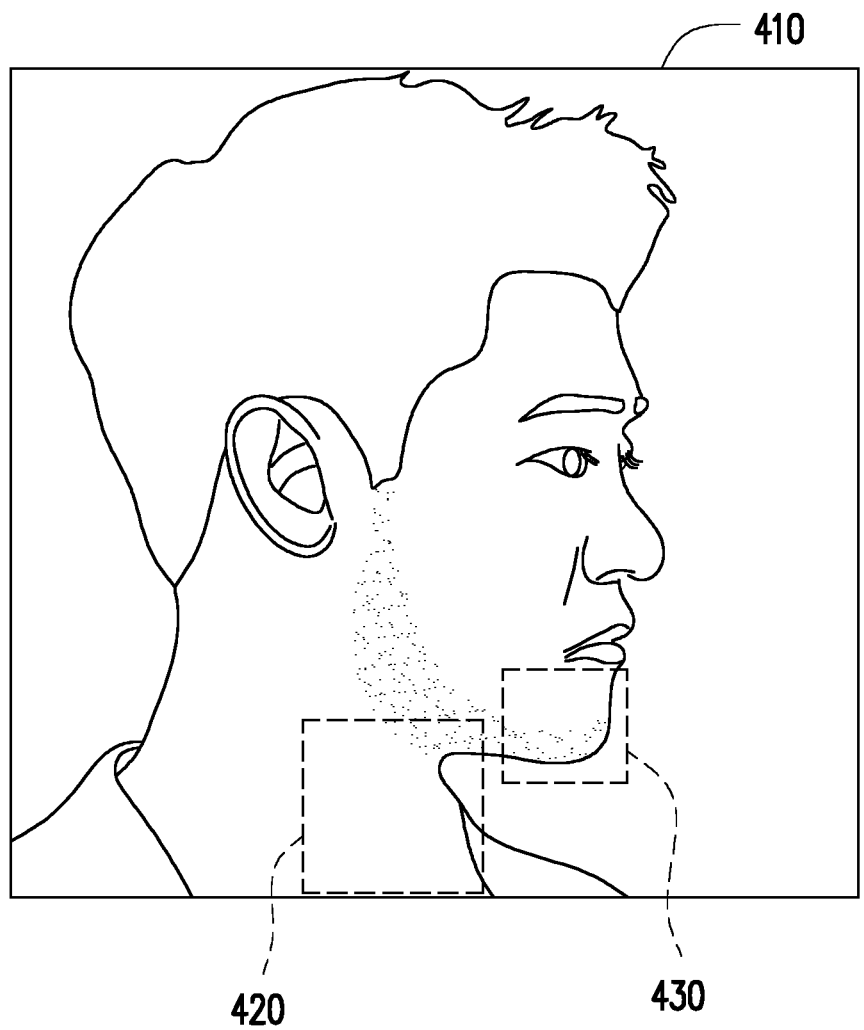
FIG. 4 illustrates ROI identification from a lateral face image in accordance with one of the exemplary embodiments of the disclosure.

FIG. 4 illustrates ROI identification from a lateral face image in accordance with one of the exemplary embodiments of the disclosure.

Referring to FIG. 4, ROIs in a lateral face image 410 may include neck 420 and chin 430.

Figure 5:
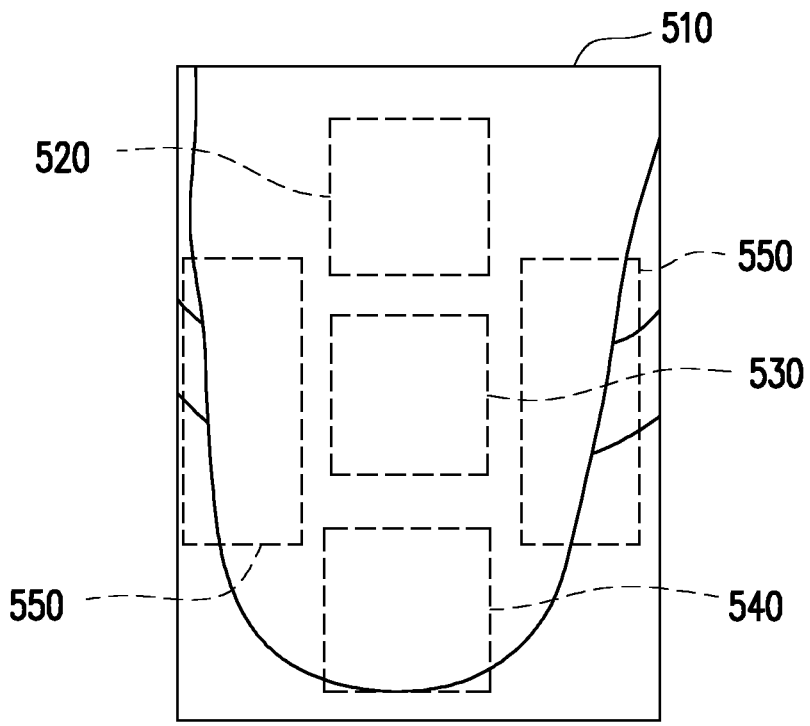
FIG. 5 illustrates ROI identification from a tongue image in accordance with one of the exemplary embodiments of the disclosure.

FIG. 5 illustrates ROI identification from a tongue image in accordance with one of the exemplary embodiments of the disclosure.

Referring to FIG. 5, ROIs in a tongue image 510 or in the frontal face image 310 may include root of tongue 520, body of tongue 530, tongue tip 540, and margin of tongue 550.

Figure 6:
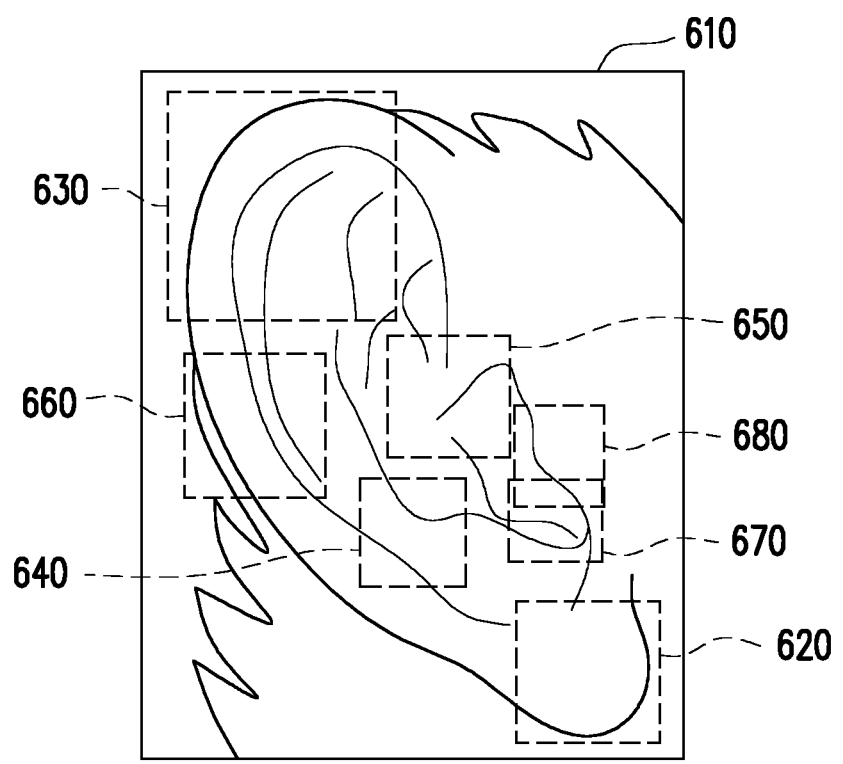
FIG. 6 illustrates ROI identification from an ear image in accordance with one of the exemplary embodiments of the disclosure.

FIG. 6 illustrates ROI identification from an ear image in accordance with one of the exemplary embodiments of the disclosure.

Referring to FIG. 6, ROIs in an ear image 610 or in the lateral face image 410 may include lobule 620, helix and triangular fossa 630, antihelix 640, concha 650, antitragus 660, external auditory meatus 670, and tragus 680.

Figure 7:
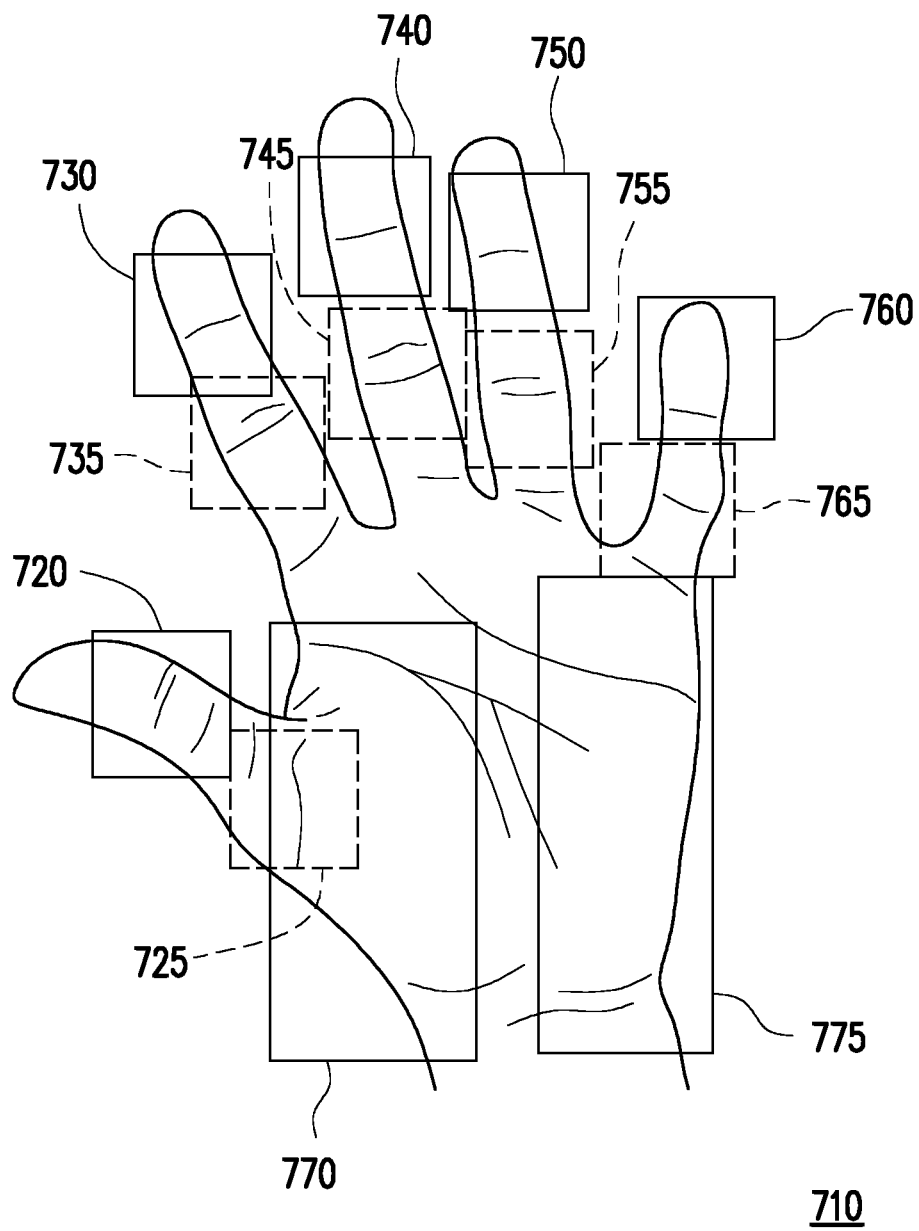
FIG. 7 illustrates ROI identification from a hand palm image in accordance with one of the exemplary embodiments of the disclosure.

FIG. 7 illustrates ROI identification from a hand palm image in accordance with one of the exemplary embodiments of the disclosure.

Referring to FIG. 7, ROIs in a hand palm image 710 may include thumb inner phalangeal joint crease 720, thumb metacarpophalangeal joint crease 725, index finger distal 730, index finger proximal 735, middle finger distal 740, middle finger proximal 745, ring finger distal 750, ring finger proximal 755, little finger distal 760, little finger proximal 765, thenar eminence 770 and hypothenar eminence 775.

Figure 8:
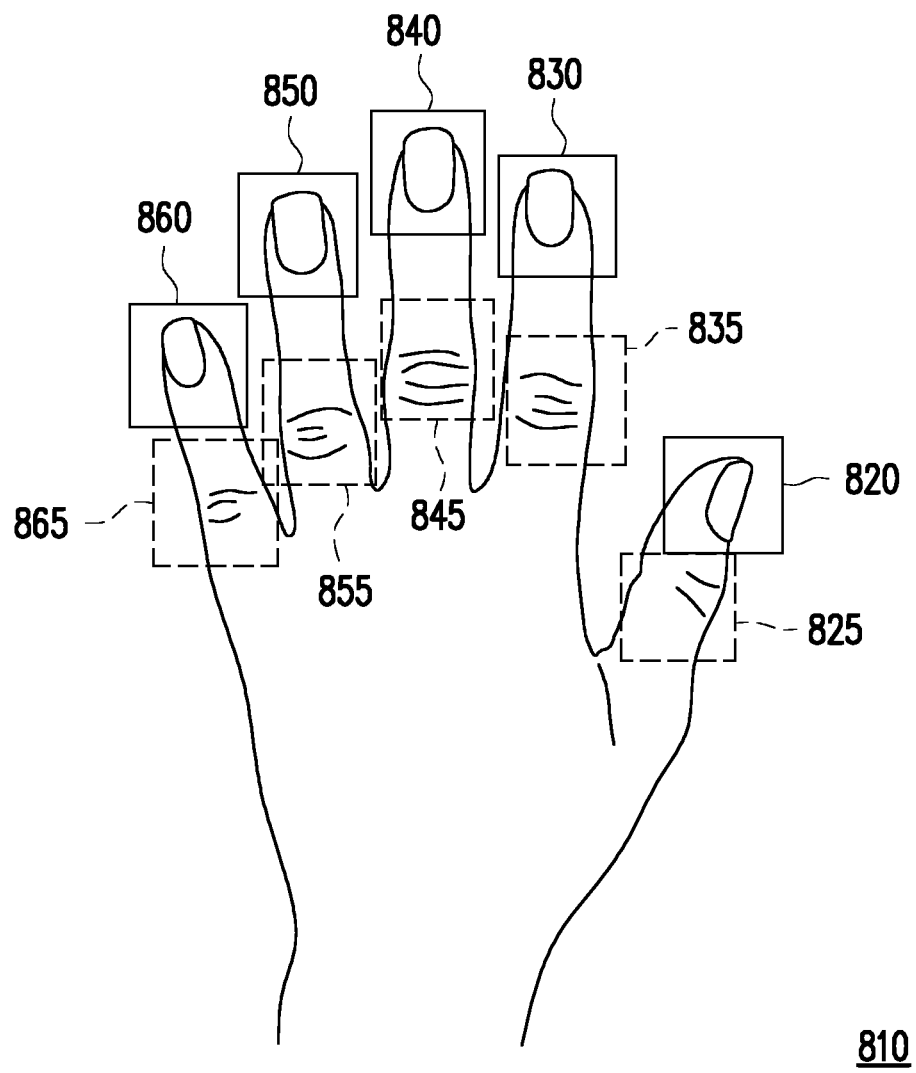
FIG. 8 illustrates ROI identification from a back of hand image in accordance with one of the exemplary embodiments of the disclosure.

FIG. 8 illustrates ROI selection from a back of hand image in accordance with one of the exemplary embodiments of the disclosure.

Referring to FIG. 8, ROIs in a back of hand image 810 may include thumb nail 820, thumb distal interphalangeal joint 825, index finger nail 830, index finger proximal interphalangeal joint 835, middle finger nail 840, middle finger proximal interphalangeal joint 845, ring finger nail 850, ring finger proximal interphalangeal joint 855, little finger nail 860, and little finger proximal interphalangeal joint 865.

Figure 9:
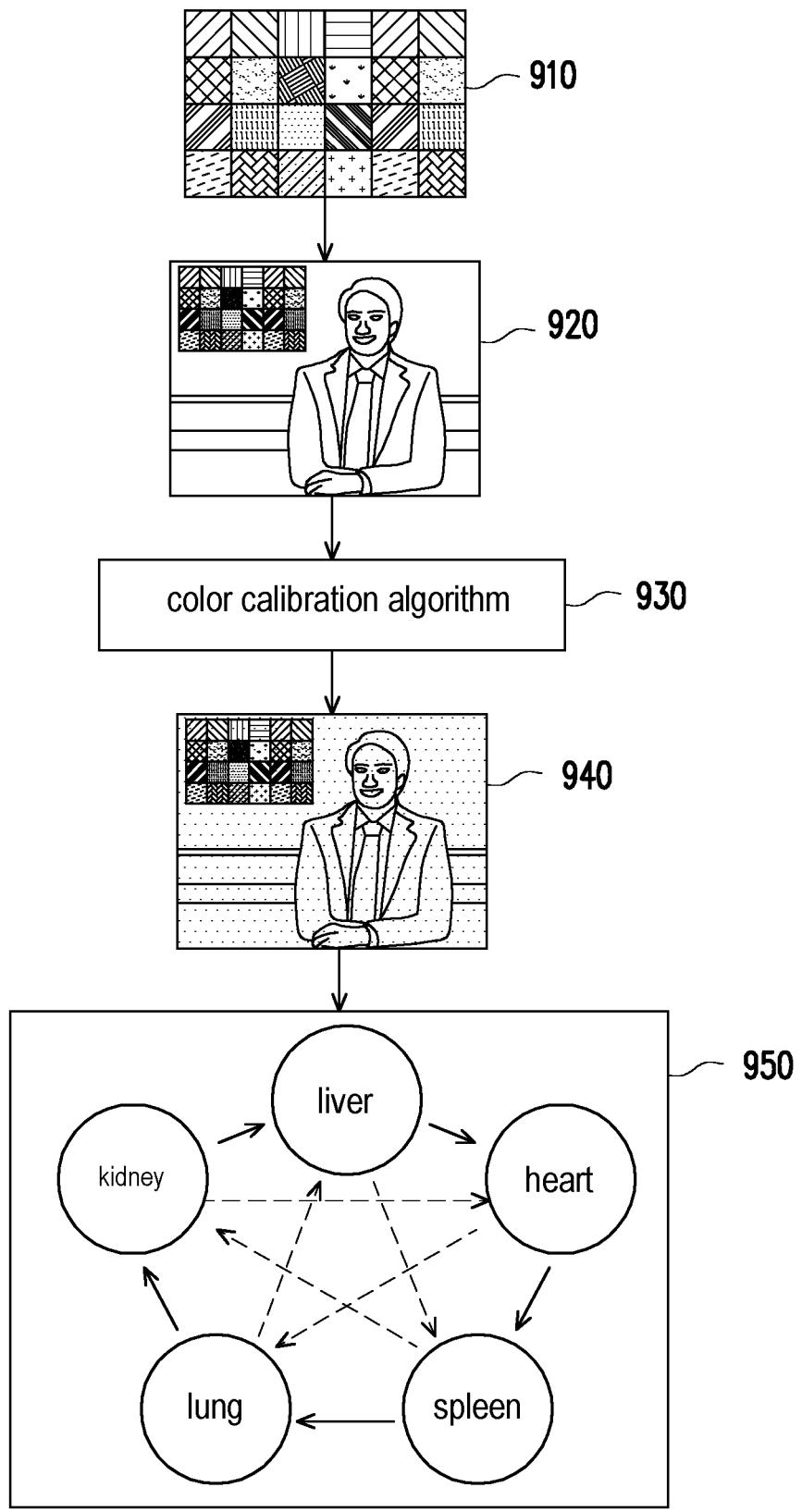
FIG. 9 illustrates a color calibration framework in accordance with one of the exemplary embodiments of the disclosure.

It should also be noted that, in some embodiments, color calibration may be a pre-processing step before clinical sign detection that is performed on the RGB image. FIG. 9 illustrates a color calibration framework in accordance with one of the exemplary embodiments of the disclosure.

Referring to FIG. 9, in order to provide an objective measurement of external skin color in captured images, a controllable light source, either in the clinic room with no or limited external light leak, as well as a color checker 910 (e.g. with a size of 24 patches) would be used during image capturing. Once an image of the examinee and the color checker 920 is captured, a color calibration algorithm 930 is applied on the captured image 920 based on the color homography mapping to generate a color calibrated image 940. The color calibration scheme is robust against different lighting conditions when examining the appearance of the examinee. It should be also noted that, in some embodiments, a color checker with a predetermined size would be also used as a relative reference to determine the size of ROIs in the captured image 920. According to the five elements theory within traditional Chinese medicine 950, five colors work at different organs and correlate with different body parts with different functions. For example, red is a color related to the heart—a face turns reddish when the cardiac activity is increased. Comparably, white is related to the lung function, yellow is related to the spleen and stomach function, green is related to the liver function, and blue is related to the kidney function. The color calibration framework would be beneficial for ensuring the color precision of the image for downstream analysis.

Figure 10:
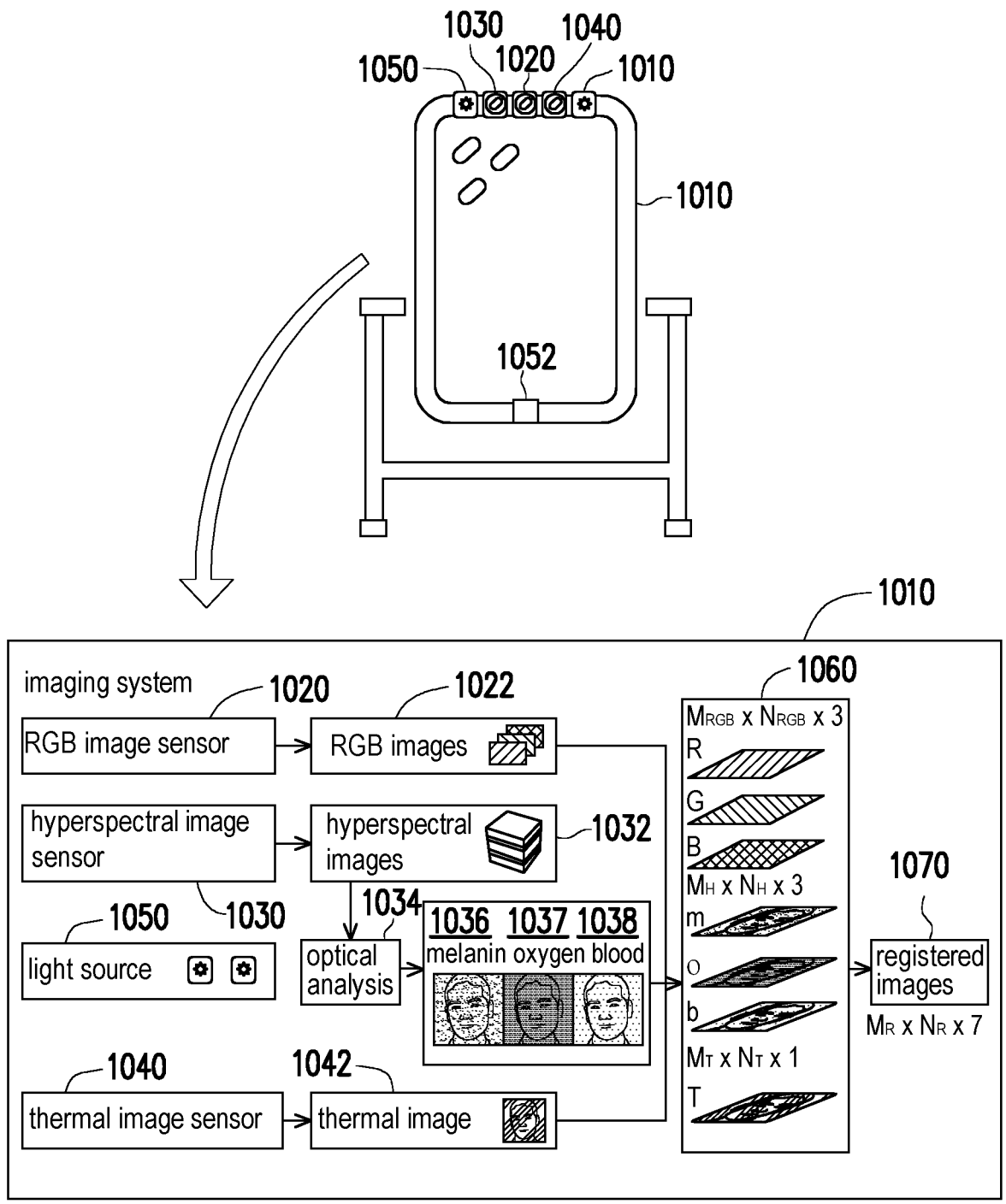
FIG. 10 illustrates a schematic diagram of an imaging system in accordance with one of the exemplary embodiments of the disclosure.

FIG. 10 illustrates a schematic diagram of an imaging system in accordance with one of the exemplary embodiments of the disclosure.

Referring to FIG. 10, a multimodality imaging system 1010, which can be in the form of a smart mirror or other type of apparatus including an RGB image sensor 1020, a hyperspectral image sensor 1030, and a thermal image sensor 1040. The RGB image sensor 1020 would capture images of the examinee and generate three channels of RGB images 1022 with high resolution images and videos of different facial and body parts. In some embodiments, a stable mirror stand may be used to minimize motions when capturing images and videos. In addition to the images which would contain color tone and morphology of the body parts, the videos would contain temporal information such as breathing patterns, eye movements, hand tremors, and so forth. The hyperspectral image sensor 1030 would capture images of the examinee and generate hyperspectral images 1032 over the visible spectrum (410 nm-700 nm) and data for 3D reconstruction sequentially within less than two seconds to collect vivo reflectance data from human skin. LED light source 1050 would be configured to acquire depth map as well as to provide sufficient illumination on the skin over the whole visible spectrum during image capturing. Sufficient illumination would be important as it serves a good base for successful color calibration. A distance sensor 1052 would be configured to measure and suggest the optimal distance according to the optical characteristics of the image sensors 1020, 1030, and 1040 to the examinee, and such distance can further provide quantitative information of morphology features. With optical analysis 1034, quantification of melanin 1036, oxygen saturation 1037, and blood/total hemoglobin 1038 are extracted to be three high-resolution images ($M_H \times N_H \times 3$ pixels). The thermal image sensor 1040 would be configured to capture images of the examinee and generate a thermal image 1042 with slight lower resolution ($M_T \times N_T \times 1$ pixels) to measure the temperature of the human skin. The three channels of RGB images from the RGB image sensor 1020, the three melanin, oxygen, and blood images from the hyperspectral image sensor 1030, and the one thermal image from the thermal image sensor 1040 would be resealed and aligned by a conventional image registration algorithm 1060, and registered images 1070 with a dimension of $M_R \times N_R \times 7$ pixels, which are generated as input data for downstream analysis. As a side note, when only the RGB sensor 1020 is used, only three channels ($M_R \times N_R \times 3$) would be used as input data for downstream analysis and image registration will not be needed. Similarly, the RGB sensor 1020 along with the thermal sensor 1040 would only result in four channels ($M_R \times N_R \times 4$) as input data for downstream analysis, and the RGB sensor 1020 along with the hyperspectral sensor 1030 would only result in six channels ($M_R \times N_R \times 6$) as input data for downstream analysis.

Figure 11:
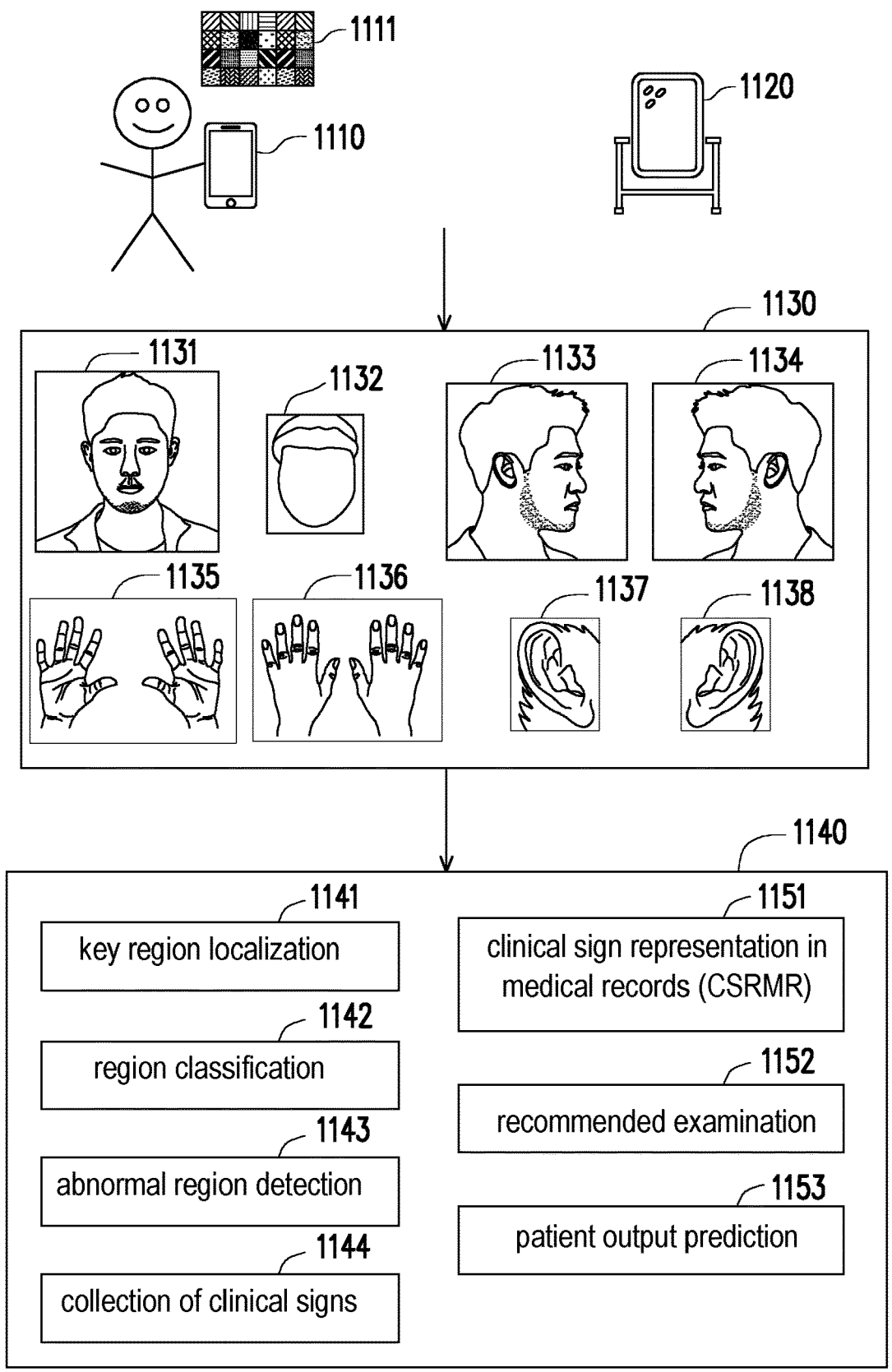
FIG. 11 illustrates a functional diagram of a platform for detecting clinical signs in accordance with one of the exemplary embodiments of the disclosure.

FIG. 11 illustrates a functional diagram of a platform for detecting clinical signs in accordance with one of the exemplary embodiments of the disclosure.

Referring to FIG. 11, an imaging system (either a monomodality optical device such as a smartphone or a tablet 1110 or a multi-modality imaging system 1120), a web server 1130, and a clinical sign detection platform 1140. In this exemplary embodiment, the clinical sign detection platform 1140 can be operated by the web server 1130. The clinical sign detection platform 1140 would include DNN-based key region localization 1141, DNN-based region classification 1142, DNN-based abnormal region detection 1143, and a collection of clinical signs 1144 would be generated. In some embodiments, an examinee may use a color checker 1111 and a guided software of the imaging system (1110 or 1120) to capture his or her images and videos of frontal face 1131, tongue close-up 1132, right side of the face 1133, left side of the face 1134, hand palms 1135, back of the hands 1136, right ear close-up 1137, and left ear close-up 1138. The frontal and lateral face images not only cover the facial area of the examinee, but also the hair, neck and shoulder which provide useful clinical information. The collected images and videos are automatically uploaded to the web server 1130. ROIs are subsequently identified by DNN-based key region localization 1141 based on modern medical knowledge. Images of health individuals and examinees with particular diseases are collected and categorized using the systems and devices disclosed herein as control and experimental groups, and DNN-based region classification algorithms 1142 is used to determine regions that are different among groups of health individuals and sick examinees. The ROIs that have discriminative power among groups may confirm existing knowledge or discover novel evidence explaining the observed clinical signs and infer the cause of the disease. In some embodiments, abnormal regions can be also detected by DNN-based abnormal region detection 1143. In some embodiments, these abnormal regions are labelled by medical experts and doctors, and would occur mostly in patients but also sometimes in healthy individuals. A collection of clinical signs 1144 are obtained by combining outputs of 1141, 1142 and 1143 as the primary outputs of the platform. These clinical signs are represented in text-based medical records by Clinical Sign Representation in Medical Records (CSRMR) 1151, and DNN-based recommended examination 1152 and patient outcome prediction 1153 will be provided as the secondary outputs of the platform. For better comprehension, more details of the clinical sign detection platform 1140 would be provided in FIGS. 12-18.

Figure 12:
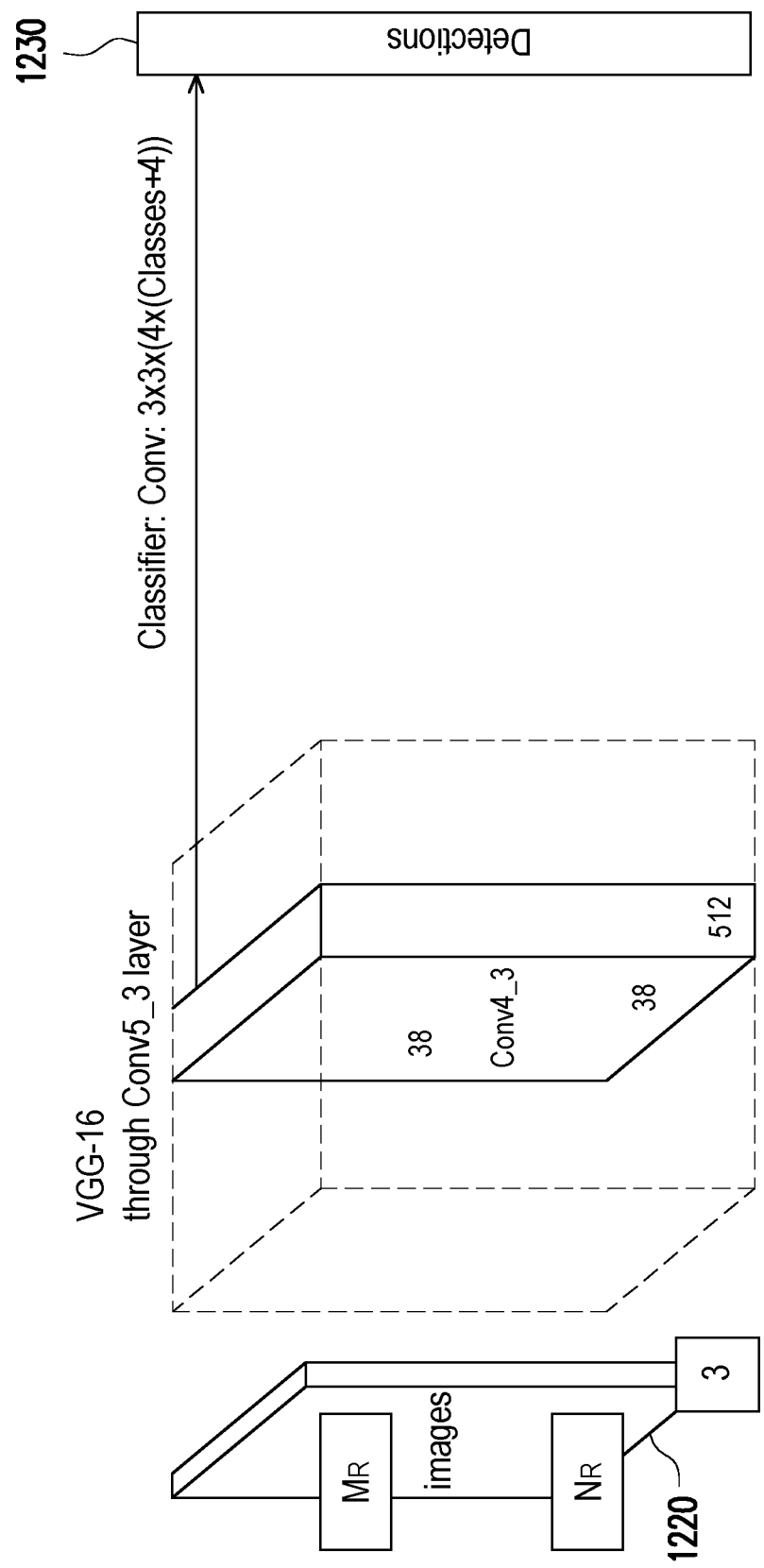
FIG. 12 illustrates a deep learning neural network based (DNN-based) framework for key region localization in accordance with one of the exemplary embodiments of the disclosure.

FIG. 12 illustrates a DNN-based framework for key region localization in accordance with one of the exemplary embodiments of the disclosure.

Referring to FIG. 12, a DNN-based region localization framework 1210 would use a well annotated datasets labelled by domain experts including physicians as well as data scientists. A DNN-based localization algorithm such as single shot multibox detector (SSD), YOLO, or a faster R-CNN may be leveraged to perform detection on the key ROIs 1230 from the registered images 1220. It should be noted that, in some embodiments, these key ROIs 1230 may have slightly different sizes due to the variation of these regions from patient to patient.

Figure 13:
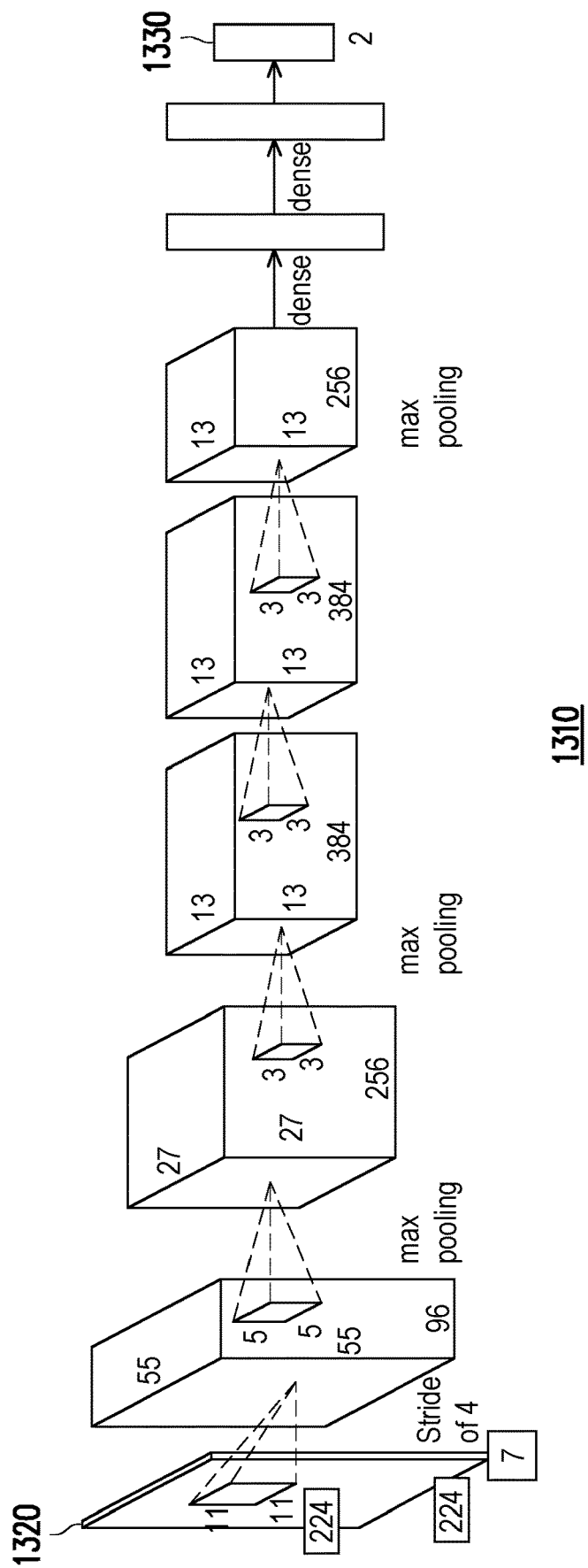
FIG. 13 illustrates a DNN-based framework for region classification in accordance with one of the exemplary embodiments of the disclosure.

FIG. 13 illustrates a DNN-based framework for region classification in accordance with one of the exemplary embodiments of the disclosure.

Referring to FIG. 13, as most state-of-the-art DNN (such as AlexNet, VGGNet and ResNet) usually uses inputs with 224×224 pixels in the first two dimensions, zero-padding is first performed on the key ROIs 1230 in FIG. 12 to make the regions square in order to retain the aspect ratio of the image features. The square region is then resized to 224×224 in the first two dimensions with 7 channels 1320 (red/green/blue channels from the RGB image sensor, thermal channel from the thermal image sensor, and melanin/oxygen/blood channels from the hyperspectral image sensor) fed into a DNN-based framework for region classification 1310 to determine the difference 1330 among groups of health individuals and patients. In some embodiments, all the 7 channels are used so as to identify important features and potential causes that may lead to the clinical signs of the patients. This region classification followed by region localization approach is applicable to all the face images, tongue and hand images demonstrated in FIGS. 3-8.

Figure 14:
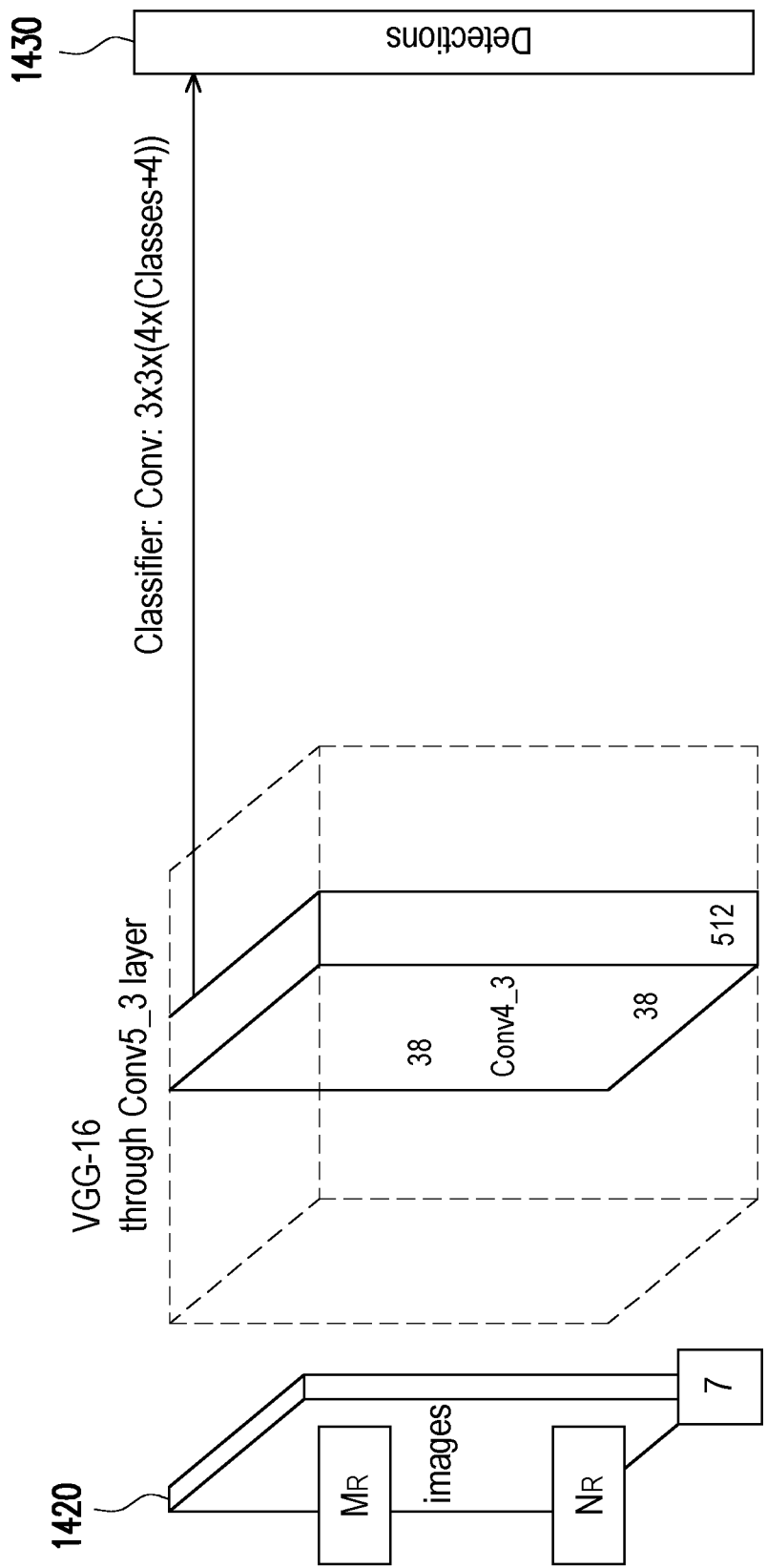
FIG. 14 illustrates a DNN-based framework for abnormal region detection in accordance with one of the exemplary embodiments of the disclosure.

FIG. 14 illustrates a DNN-based framework for abnormal region detection in accordance with one of the exemplary embodiments of the disclosure.

Referring to FIG. 14, a DNN-based abnormal region localization framework 1410 uses a well annotated datasets labelled by medical experts and doctors to identify regions on the skins or other body parts with abnormal morphology, temperature measurement, blood, oxygenation or melanin distribution as listed in Table 1, Table 2 and Table 3. Herein, Table 1 provides a list of clinical signs and medical conditions based on the HEENT examination. Table 2 provides a list of clinical signs with abnormal temperature, blood, oxygenation or melanin distribution. Table 3 provides list of clinical signs captured by all three different modalities of image sensors including RGB, thermal and hyperspectral image sensors. Then, similar to the key region localization framework 1210 in FIG. 12, the abnormal region localization framework 1410 would take the registered images 1420 and output abnormal ROIs 1430. There abnormal ROIs can be identified in both patients and healthy individuals.

TABLE 1

List of clinical signs and medical conditions based on the HEENT examination.

| Index | Body Part | Clinical Sign | Medical condition |
|---|---|---|---|
| T1-1 | Face | paleness in skin or lip | Anemia |
| T1-2 | Face | discoloration on a face | Skin rash, freckle or vitiligo |
| T1-3 | Face | distribution of discoloration on a face | Skin rash, freckle or vitiligo |
| T1-4 | Face | area of discoloration on a face | Skin rash, freckle or vitiligo |
| T1-5 | Face | humidity or flakiness of lips and tongue | Dehydration |
| T1-6 | Face | wrinkles in forehead, around eyes, and around mouth | Aging |
| T1-7 | Face | hair color | Aging |
| T1-8 | Face | acnes on a face | Skin condition |
| T1-9 | Face | distribution of acnes on a face | Skin condition |
| T1-10 | Face | number of acnes on a face | Skin condition |
| T1-11 | Face | symmetry/asymmetry of a face | Neurological diseases such as facial palsy, tics, or stroke |
| T1-12 | Face | facial round shape | Moon face |
| T1-13 | Face | size of nose and lip | Acromegaly |
| T1-14 | Face | fullness of cheek muscle | Nutritional status or cachexia |
| T1-15 | Face | focal enlargement | A tumor of specific location |

TABLE 1-continued

List of clinical signs and medical conditions based on the HEENT examination.

| Index | Body Part | Clinical Sign | Medical condition |
| --- | --- | --- | --- |
| T1-16 | Face | location of enlargement on the face | A tumor of specific location |
| T1-17 | Face | alignment of eyebrows, nose, lips and ears | Genetic disorder |
| T1-18 | Face | head position relative to neck and body | Neck muscle weakness |
| T1-19 | Face | facial expression | Pain |
| T1-20 | Face | receding hairline | Alopecia |
| T1-21 | Face | one side of the face droop downward | Bell's palsy (facial palsy) |
| T1-22 | Face | unexpected muscle spasms and the affected area's body part to twist or contort | Dystonia |
| T1-23 | Face | the neck to randomly spasm and the head to twist into uncomfortable positions | Cervical dystonia (spasmodic torticollis) |
| T1-24 | Face | trembling limbs, muscle stiffness, balance problems, and difficulty speaking | Parkinson's disease |
| T1-25 | Face | involuntary movement and verbal tics | Tourette syndrome |
| T1-26 | Eye | color tone of yellowness in eye ball (sclera) and may correlate with the serum bilirubin level | Jaundice |
| T1-27 | Eye | red color of eye ball (subconjunctival region) | Subconjunctival hemorrhage or conjunctivitis |
| T1-28 | Eye | dark areas underneath the eye and eye bags | Allergy or insomnia |
| T1-29 | Eye | eye protrusion | Eye protrusion may indicate hyperthyroidism or other eye diseases |
| T1-30 | Eye | drooping of the upper eyelid | Severity of ptosis may indicate myasthenia gravis or other eye diseases |
| T1-31 | Eye | spontaneous movement of pupil | Nystagmus or other neurological, eye, and ear diseases |
| T1-32 | Eye | yellow nodule around eyelids | Hyperlipidemia: yellowish collection of cholesterol underneath the skin, or xanthoma, which predicts hyperlipidemia |
| T1-33 | Eye | size of eyebrow | Hypothyroidism: the size shorter than eye (temporal canthus) is relevant to and can be used to indicate hypothyroidism |
| T1-34 | Eye | swelling or edematous change of periorbital region | Thyroid eye disease, allergies, or the presence of renal disease, or heart disease. |
| T1-35 | Eye | eyelid fasciculation or tremor on closed eyes | Hyperthyroidism |
| T1-36 | Eye | incapability to close the eyelid completely (lagophthalmos) | Thyroid disease or bell's palsy |
| T1-37 | Eye | twitching of eyelid | Blepharospasm |
| T1-38 | Eye | eyelid inversion (entropion) | Eye infection, inflammation, or muscle weakness |
| T1-39 | Eye | eyelid eversion (ectropion) | Muscle weakness, facial paralysis, or genetic disorders (eg. Down's syndrome) |
| T1-40 | Eye | eyelid swelling or redness | Eye infection, inflammation (eg. hordeolum, blepharitis) |
| T1-41 | Eye | triangular tissue on the cornea | Pterygium or pinguecula |
| T1-42 | Eye | the presence of a whitish, gray or blue colored arc or a circle in front of iris | Aging (eg. Senile arcus) |
| T1-43 | Eye | Eyelid Inflammation | Blepharitis |
| T1-44 | Ear | blueness in auricle | Cyanosis |
| T1-45 | Ear | pallor or redness in auricle | Vasomotor instability |
| T1-46 | Ear | tissue protrusion on the auricle | Preauricular skin tags, which is an expected variation |
| T1-47 | Ear | small whitish uric acid crystals along the peripheral margins of auricles | Gout |
| T1-48 | Ear | elevations in the periauricular skin with a punctum | Sebaceous cyst |
| T1-49 | Ear | low-set position or unusual angle | Genetic syndrome (eg. Down syndrome, Turner syndrome, Noonan syndrome, Patau syndrome, DiGeorge syndrome, Cri du chat syndrome, Edwards syndrome, and Fragile X syndrome) or renal anomalies |

TABLE 1-continued

List of clinical signs and medical conditions based on the HEENT examination.

| Index | Body Part | Clinical Sign | Medical condition |
|---|---|---|---|
| T1-50 | Nose | nasal bridge depression | Fractured nasal bone, or previous nasal cartilage inflammation |
| T1-51 | Nose | nasal flaring | Respiratory distress |
| T1-52 | Nose | nares narrowing on inspiration with mouth breathing | Chronic nasal obstruction |
| T1-53 | Mouth | dry and cracked lips | Dehydration (eg. Cheilitis) |
| T1-54 | Mouth | deep fissures at the corners of the mouth | Infection, irritation, nutritional deficiencies (iron and B vitamins) |
| T1-55 | Mouth | overclosure of the mouth | Allowing saliva to macerate the tissue |
| T1-56 | Mouth | lip swelling | Infection or allergy (angioedema) |
| T1-57 | Mouth | Lip pallor | Anemia |
| T1-58 | Mouth | circumoral pallor | Scarlet fever due to group A strep infection |
| T1-59 | Mouth | Cyanosis (bluish purple lips) | Hypoxia associated with a respiratory or cardiovascular condition |
| T1-60 | Mouth | Round, oval, or irregular bluish gray macules on the lips and buccal mucosa | Peutz-Jeghers syndrome |
| T1-61 | Mouth | Lesions, plaques, vesicles, nodules, and ulcerations | Infections, irritations, or skin cancer |
| T1-62 | Skin | color tone of paleness | Anemia |
| T1-63 | Skin | color tone of yellowness | Jaundice or carotenemia |
| T1-64 | Skin | color tone of blue | Hypoxemia |
| T1-65 | Skin | dark areas underneath the eye and eye bags | Allergy or insomnia |
| T1-66 | Skin | skin turgor/tightness or smooth surface with glare | Edema |
| T1-67 | Skin | scar | Injury |

TABLE 2

List of clinical signs with abnormal temperature, blood, oxygenation or melanin distribution

| Index | Body Part | Clinical Sign | Medical condition |
|---|---|---|---|
| T2-1 | Specific key region or any other body part | High or low temperature | Complex pain syndrome |
| T2-2 | Specific key region or any other body part | High or low temperature | Sports injury |
| T2-3 | Specific key region or any other body part | High or low temperature | Rheumatoid arthritis |
| T2-4 | Specific key region or any other body part | High or low temperature | Fever screening |
| T2-5 | Specific key region or any other body part | High or low temperature | Burn |
| T2-6 | Specific key region or any other body part | High or low temperature | Skin graft |
| T2-7 | Specific key region or any other body part | Extreme blood flow | Hemophilia or other blood flow related condition |
| T2-8 | Specific key region or any other body part | Lack of blood flow | Poor circulation or other blood flow related condition |
| T2-9 | Specific key region or any other body part | High level of oxygenation | Tumor or other oxygenation related condition |
| T2-10 | Specific key region or any other body part | Low level of oxygenation | Poor circulation or other oxygenation related condition |
| T2-11 | Specific key region or any other body part | High level of melanin | Skin pigmentation or other melanin related condition |
| T2-12 | Specific key region or any other body part | Low level of melanin | Albinos or other melanin related condition |

TABLE 3

List of clinical signs captured by all three different modalities of image sensors including RGB, thermal and hyperspectral image sensors

| Index | Body Part | Medical condition | Clinical Sign by RGB imaging - Size, shape, symmetry, lesions, morphology, alignment | Clinical Sign by Hyperspectral imaging - Blood, perfusion, oxygenation, pigmentation | Clinical Sign by Thermal imaging - temperature Inflammation, fever |
|---|---|---|---|---|---|
| T3-1 | Face | Anemia | Skin/lip color pale | Reduced blood signal | Reduced temperature |
| T3-2 | Skin | Skin cancer | Pigmentation | Pigmentation | Increase temperature |
| T3-3 | Skin | Wound | Wound shape, character | Altered blood signal | temperature change |
| T3-4 | Skin | Vasculitis | Color, characteristics | Increased blood flow | Increase temperature |
| T3-5 | Hand | Cyanosis | Skin color blue | Reduced oxygen | Reduced temperature |
| T3-6 | Leg | Peripheral arterial occlusive disease | Skin color pale | Reduced blood flow, and oxygenation | Reduced temperature |
| T3-7 | Joints | Inflammation | Joint color redness, deformity | Increased blood flow | Increased temperature |

In addition, Table 4 illustrates a collection of clinical signs and medical conditions described in Tables 1-3. This list is termed as Clinical Sign Representation in Medical Records (CSRMR), a novel representation of clinical signs in text-based medical records and can be reviewed for each patient. With CSRMR representation from image-based clinical signs into text-based medical records, it is now feasible to apply DNN or other machine learning approaches for recommended examinations and predicted outcomes.

TABLE 4

A collection of clinical signs and medical conditions described in Tables 1-3

| Index | Body Part | Clinical Sign | Medical condition | Patient Check |
|---|---|---|---|---|
| T1-1 | Face | paleness in skin or lip | Anemia | Yes or No |
| T1-2~67 | ... | ... | ... | Yes or No |
| T2-1 | Specific key region or any other body part | High or low temperature | Complex pain syndrome | Yes or No |
| T2-2~12 | ... | ... | ... | Yes or No |
| T3-1 | Face | Skin/lip color, low level of blood, poor perfusion, lower temperature | Anemia | Yes or No |
| T3-2~7 | ... | ... | ... | Yes or No |

Figure 15:
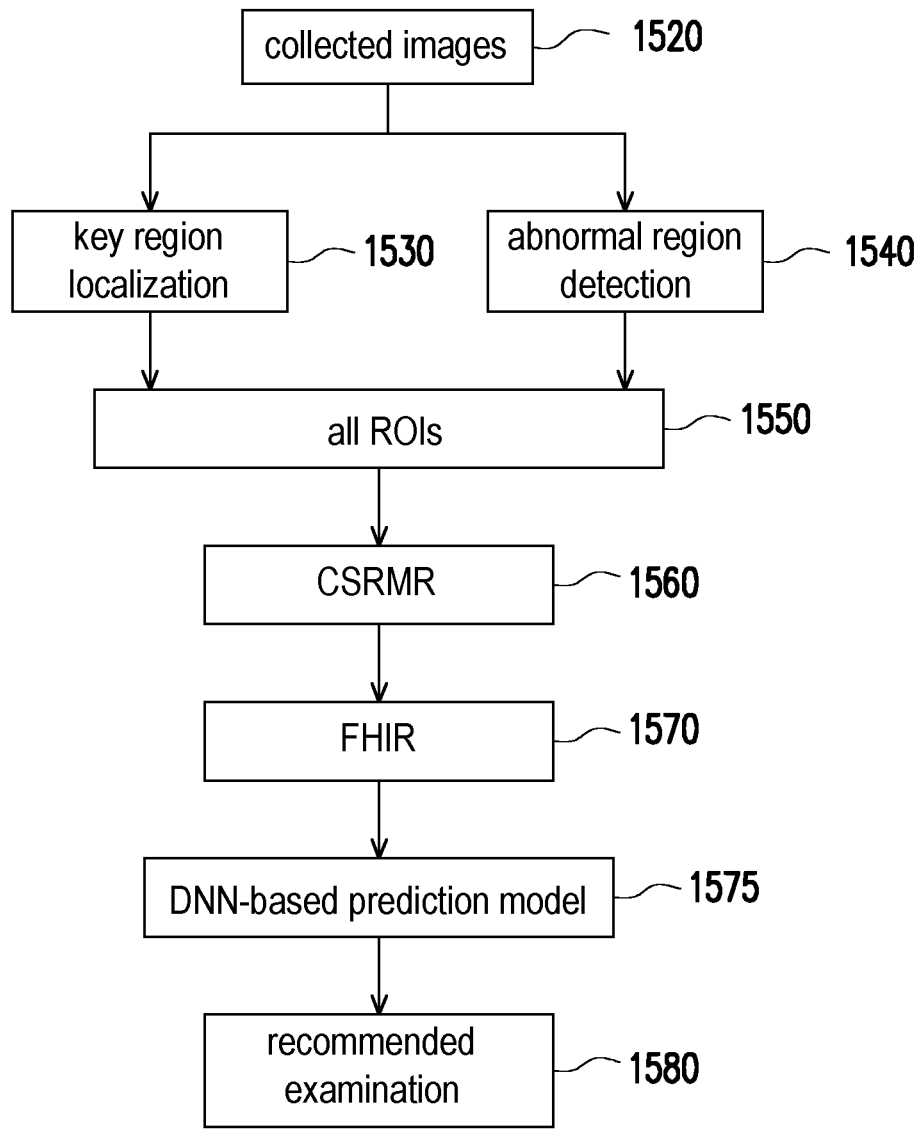
FIG. 15 illustrates an ensemble recommendation system for further examination in accordance with one of the exemplary embodiments of the disclosure.

FIG. 15 illustrates an ensemble recommendation system for further examination 1510 in accordance with one of the exemplary embodiments of the disclosure.

Referring to FIG. 15, given collected images 1520, all ROIs 1550 would be identified through key region localization 1530 and abnormal region detection 1540, and these image-based ROIs can be converted into new set of text-based medical records by CSRMR 1560, and these information can be further represented in Fast Healthcare Interoperability Resources (FHIR) format 1570 (referred to as "FHIR-format medical record" hereafter). FHIR is a popular data representation to represent raw Electronic Health Record (EHR) data in a consistent, hierarchical, and flexible manner for patient outcome prediction. With this representation as input, a DNN-based prediction model 1575 or other machine learning classifiers (such as Self Organizing Maps) produce a recommended examination 1580 for the patient. This ensemble recommendation system uses a well annotated datasets labelled by medical experts and doctors to identify recommended examinations for patient with specific medical conditions.

Figure 16:
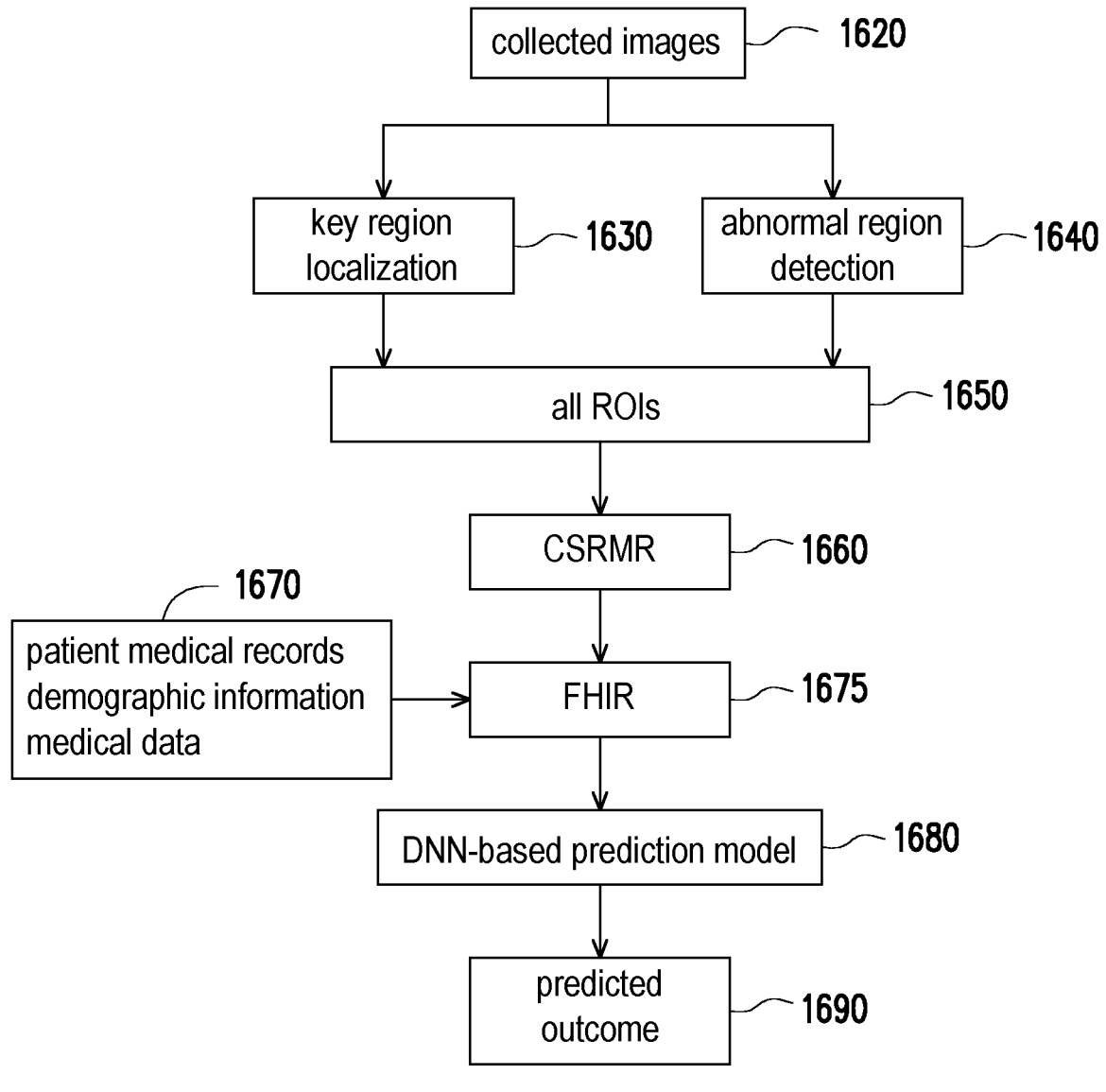
FIG. 16 illustrates an outcome prediction framework of a patient in accordance with one of the exemplary embodiments of the disclosure.

FIG. 16 illustrates an outcome prediction framework of a patient 1610 in accordance with one of the exemplary embodiments of the disclosure.

Referring to FIG. 16, given collected images 1620, all ROIs 1650 would be identified through key region localization 1630 and abnormal region detection 1640, and these ROIs can be converted to new set of medical records by CSRMR 1660. Such information can be combined with original medical records of the patient, including demographic information and medical data 1670, to be further represented in a FHIR format 1675. The FHIR-format medical records would be fed into a DNN-based prediction model 1680 or other machine learning classifiers (such as recurrent neural network-based framework) to output a predicted outcome 1690 of the patient such as mortality, readmissions, long length of stay, inferring discharge diagnoses, or other patient outcome measurements.

Figure 17:
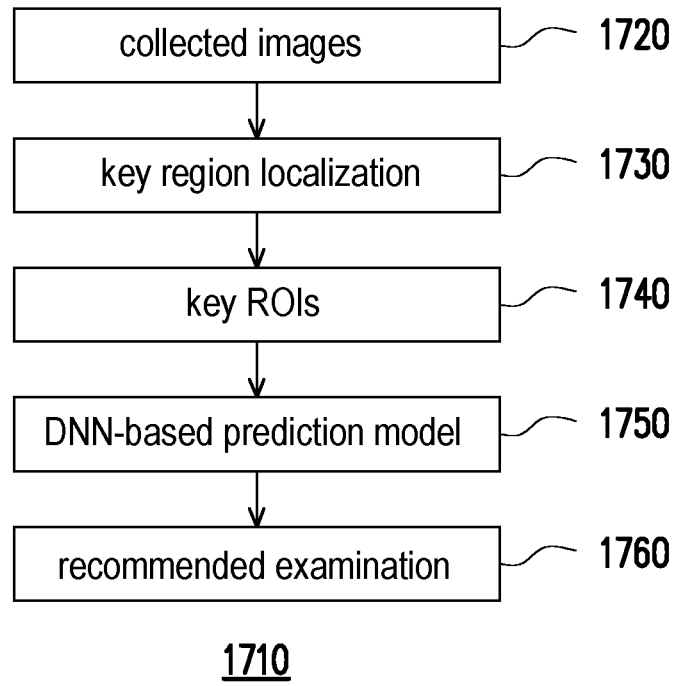
FIG. 17 illustrating a simplified ensemble recommendation system for further examination in accordance with one of the exemplary embodiments of the disclosure.

FIG. 17 illustrating a simplified ensemble recommendation system for further examination 1710 in accordance with one of the exemplary embodiments of the disclosure.

Referring to FIG. 17, given collected images 1720, all key ROIs 1740 would be identified through key region localization 1730. Without abnormal ROIs where the number of images may vary from patient to patient, the key ROIs can be fed into a DNN-based prediction model 1750 or other machine learning classifiers (such as Self Organizing Maps) to produce a recommended examination 1760. Similar to FIG. 15, this ensemble recommendation system uses a well annotated datasets labelled by medical experts and doctors to identify recommended examinations for patient with specific medical conditions.

Figure 18:
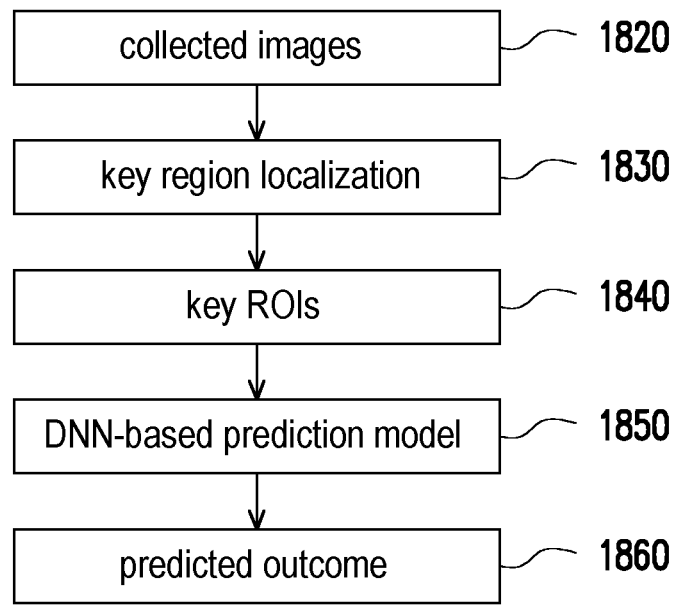
FIG. 18 illustrating a simplified outcome prediction framework of a patient in accordance with one of the exemplary embodiments of the disclosure.

FIG. 18 illustrating a simplified outcome prediction framework of a patient 1810 in accordance with one of the exemplary embodiments of the disclosure.

Referring to FIG. 18, given collected images 1820, all key ROIs 1840 would be identified through key region localization 1830. Without abnormal ROIs where the number of images may vary from patient to patient, the key regions of interests can be fed into a DNN-based prediction model 1850 or other machine learning classifiers (such as recurrent neural network-based framework) to output a predicted outcome 1860 of the patient such as mortality, readmissions, length of stay, inferring discharge diagnoses, or other patient outcome measurements.

As illustrated above, the imaging system may be a monomodality optical device such as consumer-grade RGB camera on smartphones or tablets, or may be a more comprehensive imaging apparatus with additional modalities such as a thermal image sensor and/or hyperspectral image sensor in accordance with some embodiments. Clinical signs may be obtained from the general appearance of a patient's head, eyes, ears, nose, throat/mouth, tongue, neck, hand, extremities, skin and any body parts which could provide important clues to evaluate the underlying medical conditions. The former system could potentially cover the list of clinical signs demonstrated in Table 1.

In utilization, the systems and devices disclosed herein are widely used for individuals at home before visiting clinics and hospitals, and used at senior center and nursing home as for telemedicine. Further, it can be used by the physicians to record the inspection by images (rather than written texts), which provides more accurate, transferrable, and are able to be compared serially. The later system is more comprehensive and could detect additional clinical signs listed in Table 2 and Table 3. With a more sophisticated and expensive system in some embodiments, it is used in medical centers and teaching hospitals and provide critical information for precision health and precision medicine. Compared to other prior studies, the system disclosed here could detect a more variety and comprehensive collection of clinical signs based on both images and videos as well as machine learning analytics such as DNN-based computational models for further recommend examinations and outcome predictions.

In operation, capturing an image of a patient by using the RGB image sensor to generate an RGB image and detecting clinical signs of the patient by the processing device is based on the RGB image.

In view of the aforementioned descriptions, the imaging system and method may be used to detect informative clinical signs based on the HEENT examination and any body part which may reveal subtle and critical information related to a patient's health condition, which enables the patient to understand his/her health condition and discover the early stage of diseases by a non-invasive and convenient manner.

No element, act, or instruction used in the detailed description of disclosed embodiments of the present application should be construed as absolutely critical or essential to the present disclosure unless explicitly described as such. Also, as used herein, each of the indefinite articles "a" and "an" could include more than one item. If only one item is intended, the terms "a single" or similar languages would be used. Furthermore, the terms "any of" followed by a listing of a plurality of items and/or a plurality of categories of items, as used herein, are intended to include "any of", "any combination of", "any multiple of", and/or "any combination of multiples of the items and/or the categories of items, individually or in conjunction with other items and/or other categories of items. Further, as used herein, the term "set" is intended to include any number of items, including zero. Further, as used herein, the term "number" is intended to include any number, including zero.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A method of clinical sign detection, applicable to an imaging system having an RGB image sensor, a processor, a memory with a medical database and a light source and a color checker with a plurality of different color patches, comprising:
    controlling the light source;
    capturing an image of a patient or examinee and the plurality of different color patches by the RGB image sensor;
    calibrating color of the captured image of the patient or examinee based on the image of the plurality of different color patches under different lighting conditions to generate an RGB image; and
    detecting clinical signs of the patient or examinee based on the RGB image by the processor, wherein the detecting clinical signs of the patient or examinee based on the RGB image comprises:
    identifying at least one key region of interest (ROI) from the RGB image by a DNN-based key region localization framework based on the medical database through one of a single shot multibox detector (SSD), a YOLO, and a faster R-CNN, wherein the DNN-based key region localization framework uses a well annotated datasets labelled by medical experts and doctors;
    feeding each RGB channel corresponding to the key ROI into a DNN-based framework for region classification to determine differences between healthy individuals and examinees with particular diseases based on images of the healthy individuals, wherein the images of the healthy individuals are previously collected and categorized from a plurality of specific body parts of the healthy individuals, wherein the plurality of specific body parts comprise face, tongue, ear and hand;
    determining at least one abnormal ROI from the RGB image through a DNN-based abnormal region localization framework based on the differences between the healthy individuals and the examinees with particular diseases, wherein the DNN-based abnormal region localization framework uses a well annotated datasets labelled by medical experts and doctors; and
    identifying the clinical signs based on at least one of the key ROI and the abnormal ROI, and converting the at least one key ROI and the at least one abnormal ROI to a text-based medical record.

2. The method according to claim 1, wherein after the step of generating the RGB image, the method further comprises:
    setting the RGB image in each RGB channel as inputs for detecting the clinical signs of the patient or examinee.

3. The method according to claim 1, wherein after the step of generating the RGB image, the method further comprises:
    extracting melanin components and hemoglobin components from the RGB image to generate a melanin image and a hemoglobin image;
    setting the RGB image in each RGB channel, the melanin image, and the hemoglobin image as inputs for detecting the clinical signs of the patient or examinee.

4. The method according to claim 1 further comprises:
feeding the at least one key ROI to a machine learning classifier to produce a predicted outcome of the patient or examinee.

5. The method according to claim 1 further comprises:
feeding the at least one key ROI to a machine learning classifier to produce a recommended examination for the patient or examinee.

6. The method according to claim 1 further comprises:
converting the text-based medical record to a FHIR-format medical record; and
feeding the FHIR-format medical record to a machine learning classifier to produce a recommended examination for the patient or examinee.

7. The method according to claim 1 further comprises:
obtaining an original medical record of the patient or examinee, wherein the original medical record comprises demographic information and medical data;
combining and converting the text-based medical record and the original medical record to a combined FHIR-format medical record; and
feeding the FHIR-format medical record to a machine learning classifier to produce a predicted outcome of the patient or examinee.

8. The method according to claim 1, wherein the imaging system further comprises a thermal image sensor, and wherein the method further comprises:
capturing an image of the patient or examinee by the thermal image sensor to generate a thermal image.

9. The method according to claim 8, wherein after the step of generating the RGB image, the method further comprises:
setting the RGB image in each RGB channel and the thermal image as inputs for detecting the clinical signs of the patient or examinee.

10. The method according to claim 1, wherein the imaging system further comprises a hyperspectral image sensor, and wherein the method further comprises:
capturing an image of the patient or examinee by the hyperspectral image sensor to generate a hyperspectral image.

11. The method according to claim 10, wherein after the step of generating the RGB image, the method further comprises:
extracting a melanin volume fraction, total hemoglobin volume fractions, and oxygen saturation from the hyperspectral image to generate the melanin image, the oxygen image, and the blood image;
setting the RGB image in each RGB channel, the melanin image, the oxygen image, and the blood image as inputs for detecting the clinical signs of the patient or examinee.

12. The method according to claim 1, wherein the imaging system further comprises a thermal image sensor and a hyperspectral image sensor, and wherein the method further comprises:
capturing images of the patient or examinee by the thermal image sensor and the hyperspectral image sensor to respectively generate a thermal image and a hyperspectral image.

13. The method according to claim 12, wherein after the step of generating the RGB image, the method further comprises:
extracting a quantification of melanin, oxygen saturation, and blood/total hemoglobin from the hyperspectral image to generate the melanin image, the oxygen image, and the blood image;
setting the RGB image in each RGB channel, the thermal image, the melanin image, the oxygen image, and the blood image as inputs for detecting the clinical signs of the patient or examinee.

14. The method according to claim 1, wherein the color checker with a predetermined size is used as a relative reference to determine a size of at least one region of interest (ROI) in the captured image.

15. The method according to claim 1, wherein the imaging system further comprises a distance sensor, and wherein before the step of capturing the image of the patient or examinee by the RGB image sensor, the method further comprises:
suggesting an optimal distance between the RGB sensor and the patient or examinee by the distance sensor.

16. The method according to claim 1, wherein the RGB image is an HEENT image or any other body parts' image.

17. An imaging system comprising:
an RGB image sensor, configured to capture an image of a patient or examinee to generate an RGB image;
a memory, configured to store a medical database;
a processor, configured to obtain the RGB image from the RGB image sensor and detect clinical signs of the patient or examinee based on the RGB image;
a light source, controllable during image capturing; and
a color checker with a plurality of different color patches, wherein the RGB image sensor captures an image of the patient or examinee and the plurality of different color patches;
wherein the processor is further configured to
calibrating color of the captured image of the patient or examinee based on the image of the plurality of different color patches under different lighting conditions to generate an RGB image; and
detecting clinical signs of the patient or examinee based on the RGB image, wherein the detecting clinical signs of the patient or examinee based on the RGB image comprises:
identifying at least one key region of interest (ROI) from the RGB image by a DNN-based key region localization framework based on the medical database through one of a single shot multibox detector (SSD), a YOLO, and a faster R-CNN, wherein the DNN-based key region localization framework uses a well annotated datasets labelled by medical experts and doctors;
feeding each RGB channel corresponding to the key ROI into a DNN-based framework for region classification to determine differences between healthy individuals and examinees with particular diseases based on images of the healthy individuals, wherein the images of the healthy individuals are previously collected and categorized from a plurality of specific body parts of the healthy individuals, wherein the plurality of specific body parts comprise face, tongue, ear and hand;
determining at least one abnormal ROI from the RGB image through a DNN-based abnormal region localization framework based on the differences between the healthy individuals and the examinees with particular diseases, wherein the abnormal region localization framework uses a well annotated datasets labelled by medical experts and doctors; and
identifying the clinical signs based on at least one of the key ROI and the abnormal ROI, and converting the at least one key ROI and the at least one abnormal ROI to a text-based medical record.

18. The imaging system according to claim 17 further comprises:
   a thermal image sensor, configured to capture an image of the patient or examinee to generate a thermal image for detecting the clinical signs.

19. The imaging system according to claim 17 further comprises:
   a hyperspectral image sensor, configured to capture an image of the patient or examinee to generate a hyperspectral image for detecting the clinical signs.

20. The imaging system according to claim 17 further comprises:
   a distance sensor, configured to measure a distance between the RGB sensor and the patient or examinee and suggest an optimal distance between the RGB sensor and the patient or examinee.

* * * * *